United States Patent
Ko

(10) Patent No.: US 12,114,834 B2
(45) Date of Patent: Oct. 15, 2024

(54) METHOD OF DETECTING COLON POLYPS THROUGH ARTIFICIAL INTELLIGENCE-BASED BLOOD VESSEL LEARNING AND DEVICE THEREOF

(71) Applicant: Jihwan Ko, Busan (KR)

(72) Inventor: Jihwan Ko, Busan (KR)

( * ) Notice: Subject to any disclaimer, the term of this patent is extended or adjusted under 35 U.S.C. 154(b) by 398 days.

(21) Appl. No.: 17/720,817

(22) Filed: Apr. 14, 2022

(65) Prior Publication Data

US 2023/0225584 A1 Jul. 20, 2023

Related U.S. Application Data

(63) Continuation of application No. PCT/KR2022/001942, filed on Feb. 8, 2022.

(30) Foreign Application Priority Data

Jan. 19, 2022 (KR) .......................... 10-2022-0007724

(51) Int. Cl.
*A61B 1/00* (2006.01)
*A61B 1/31* (2006.01)
*G16H 30/40* (2018.01)
*G16H 50/20* (2018.01)

(52) U.S. Cl.
CPC .. *A61B 1/000096* (2022.02); *A61B 1/000094* (2022.02); *A61B 1/00045* (2013.01); *A61B 1/31* (2013.01); *G16H 30/40* (2018.01); *G16H 50/20* (2018.01)

(58) Field of Classification Search
CPC ....... A61B 1/00; A61B 1/31; A61B 1/000094; A61B 1/00045; A61B 1/000096; G16H 30/40; G16H 50/20
See application file for complete search history.

(56) References Cited

U.S. PATENT DOCUMENTS 11,756,191 B2 * 9/2023 Wang .................... G06T 11/005
382/131

FOREIGN PATENT DOCUMENTS

KR 10-2037303 B1 10/2019

* cited by examiner

*Primary Examiner* — Tuan H Nguyen
(74) *Attorney, Agent, or Firm* — Studebaker & Brackett PC

(57) ABSTRACT

A method of detecting colon polyps disclosed in the present disclosure includes: (a) receiving an image captured by an endoscope inserted into colon of a test subject; (b) recognizing each image section including colonic mucosa and colonic blood vessels in the image; (c) determining whether a colonic vascular bed is disconnected in each image section; (d) displaying a first visual effect representing a vascular bed in which the colonic blood vessels are disconnected; and (e) displaying a second visual effect representing a continuous vascular bed of the colonic blood vessels, wherein operation (b) is configured to recognize each image section through a deep learning model, which is machine learned based on blood vessel data in a plurality of colonic images of the test subject obtained from external annotators, and a degree of disconnection of the vascular bed and a blood vessel pattern.

10 Claims, 6 Drawing Sheets

METHOD OF DETECTING COLON POLYPS THROUGH ARTIFICIAL INTELLIGENCE-BASED BLOOD VESSEL LEARNING AND DEVICE THEREOF

CROSS-REFERENCE TO RELATED APPLICATION

The present application is a continuation of International Patent Application No. PCT/KR2022/001942, filed on Feb. 8, 2022, which is based upon and claims the benefit of priority to Korean Patent Application No. 10-2022-0007724 filed on Jan. 19, 2022. The disclosures of the above-listed applications are hereby incorporated by reference herein in their entirety.

BACKGROUND

1. Technical Field

The present disclosure relates to a method and device for detecting colon polyps, and more particularly, to a method and device for detecting colon polyps through artificial intelligence-based blood vessel learning.

2. Description of Related Art

Recently, the incidence of colon cancer in Korea has been rapidly increasing due to a westernized diet and lack of exercise.

80-90% of colon cancer starts with a polyp (adenoma), a small lump in the colon.

According to one statistic, there is also a report that when such a polyp is detected and removed early through colonoscopy, the mortality rate from colon cancer may be reduced by 66%.

Professional medical staff diagnose a disease of a test subject through various tests and suggest treatment.

In some cases, for a more accurate diagnosis, a radiographic image or a pathological image scanned from a tissue slide is read.

However, it is very difficult for the human eye to find an abnormal site with a size of 100×100 pixels in an image with a size of 100,000×100,000 pixels.

It is not easy to distinguish tumor tissue from normal tissue with the naked eye, even for a skilled surgeon who has undergone a training course, and depending on the image, it may take tens of minutes to several hours to analyze.

In addition, it is often the case that anomalous cases are missed.

Because the colon is long and has severe curves and numerous wrinkles, it is very difficult for a skilled surgeon to completely observe the surface of an inner wall of the colon.

In particular, it is not easy to find thin and flat thin-film planar polyps existing on the colonic mucosa with a normal level of skill, and it is difficult to easily distinguish cancer cells with a size of about 1 mm or minute changes in the colonic mucosa with the naked eye.

In addition, since it is a difficult task to check with the human eye, there may be human errors. Hence, there are also many cases where different diagnoses are made for the same test subject.

Given the large amount of information that a specialist surgeon needs to review within a limited time, the possibility of a misdiagnosis cannot be completely ruled out.

Typically, as the cause of cancer misdiagnosis damage, it is known that the response rate of neglecting additional tests or reading errors is the highest.

In addition, as the size of a polyp is small or thin, the overlooked rate tends to increase, and cases of colon cancer diagnosed within several years of receiving a normal colonoscopy diagnosis often occur.

In addition, the possibility that the image may not be seen perfectly cannot be completely excluded, depending on elements such as resolution, contrast ratio, and luminance supported by a colonoscopy image reading monitor.

A colonoscopy image reading monitor needs to essentially support elements such as high resolution of at least 8-bit condition, but in reality, it is expensive equipment, so there is a limit to purchase or use thereof.

In order to overcome this limitation and read medical images more efficiently, artificial intelligence (AI) technologies such as deep learning have been recently introduced into the field of diagnosis using medical images.

AI technology based on machine learning such as deep learning is the basis for bringing about a leap forward in accurately diagnosing a disease of a test subject using medical images.

Therefore, the present inventors have come to invent a method and device for detecting colon polyps through AI-based blood vessel learning capable of recognizing each image section including colonic mucosa and colonic blood vessels within a colonoscopy image using AI, and creating a deep learning model for the disconnection of a vascular bed in the colon so that even a colonoscopy tester with low test proficiency can accurately detect thin, flat, thin-film planar polyps existing on the colonic mucosa.

SUMMARY

An aspect of the present disclosure is directed to providing a method of detecting colon polyps through AI-based blood vessel learning, wherein the method uses AI that has learned the shape of a colic vasculature to detect a pattern in which a vascular bed seen between the colonic mucosa is disconnected, centered on a marked line and discriminate the same as a suspicious lesion.

Another aspect of the present disclosure is directed to providing a device for detecting colon polyps through AI-based blood vessel learning.

A method of detecting colon polyps through AI-based blood vessel learning according to an embodiment of the present disclosure is performed by a device, and includes: (a) receiving an image captured by an endoscope inserted into the colon of a test subject in real time; (b) recognizing each image section including colonic mucosa and colonic blood vessels in the image; (c) determining whether a colonic vascular bed is disconnected in each image section; (d) displaying a first visual effect representing a vascular bed in which the colonic blood vessels are disconnected in each image section; and (e) displaying a second visual effect representing a continuous vascular bed of the colonic blood vessels in each image section, wherein operation (b) is configured to recognize each image section through a deep learning model, and wherein the deep learning model is a machine-learning model based on blood vessel data in a plurality of colonic images of the test subject obtained from external annotators, and a degree of disconnection of the vascular bed due to light irradiated into an interior of the colon and a blood vessel pattern.

The first visual effect of the method of detecting colon polyps through AI-based blood vessel learning according to an embodiment of the present disclosure includes a visual effect in which each marker is displayed on the corresponding vascular bed in which the colonic blood vessels are disconnected in each image section.

The size of each of the markers of the method of detecting colon polyps through AI-based blood vessel learning according to an embodiment of the present disclosure is determined based on a degree of disconnection of the corresponding vascular bed.

In the method of detecting colon polyps through AI-based blood vessel learning according to an embodiment of the present disclosure, a control unit is configured to determine a presence and size of thin-film planar polyps on colonic mucosa through the first visual effect, and determine an absence of the thin-film planar polyps on the colonic mucosa through the second visual effect.

In operation (c) of the method of detecting colon polyps through AI-based blood vessel learning according to an embodiment of the present disclosure, whether the colonic vascular bed is disconnected is determined based on whether a degree of disconnection of the corresponding vascular bed changes by more than a preset percentage threshold value. When the degree of disconnection of the vascular bed is greater than or equal to the preset percentage threshold value, the control unit determines that there is a thin-film planar polyp on a corresponding area on the colonic mucosa.

The method of detecting colon polyps through AI-based blood vessel learning according to an embodiment of the present disclosure is stored as a computer program in a computer-readable recording medium in order to be performed in combination with a computer, which is hardware.

A device for detecting colon polyps through AI-based blood vessel learning according to another embodiment of the present disclosure includes: a display unit; a communication unit receiving an image captured by an endoscope inserted into colon of a test subject in real time; a storage unit storing the received image and a deep learning model for recognizing colonic blood vessels in the received image; and a control unit recognizing each image section including colonic mucosa and colonic blood vessels in the received image through the deep learning model, displaying, on the display unit, a first visual effect representing a vascular bed in which the colonic blood vessels are disconnected in each image section, and displaying, on the display unit, a second visual effect representing a continuous vascular bed of the colonic blood vessels in each image section, wherein the deep learning model is a machine-learning model based on blood vessel data in a plurality of colonic images of the test subject obtained from external annotators, and a degree of disconnection of the vascular bed due to light irradiated into an interior of the colon and a blood vessel pattern.

The first visual effect of the device for detecting colon polyps through AI-based blood vessel learning according to another embodiment of the present disclosure includes a visual effect in which each marker is displayed on the corresponding vascular bed in which the colonic blood vessels are disconnected in each image section, and the size of each of the markers is determined based on a degree of disconnection of the corresponding vascular bed.

The control unit of the device for detecting colon polyps through AI-based blood vessel learning according to another embodiment of the present disclosure is configured to determine a presence and size of thin-film planar polyps on colonic mucosa through the first visual effect, and determine an absence of the thin-film planar polyps on the colonic mucosa through the second visual effect.

The control unit of the device for detecting colon polyps through AI-based blood vessel learning according to another embodiment of the present disclosure determines whether the vascular bed is disconnected based on whether a degree of disconnection of the corresponding vascular bed changes by more than a preset percentage threshold value. When the degree of disconnection of the vascular bed is greater than or equal to the preset percentage threshold value, the control unit determines that there is a thin-film planar polyp on a corresponding area on the colonic mucosa.

Other specific details of the present disclosure are included in the detailed description and drawings.

According to the present disclosure, when reading a colon disease through a colonoscopy image, even a colonoscopy tester with low test proficiency will be able to detect and excise polyps with high accuracy for abnormal colon lesions where thin, flat, thin-film planar polyps existing on the colonic mucosa are hidden.

The advantages of the present disclosure are not limited to those mentioned above, and other advantages not mentioned herein will be clearly understood by those skilled in the art from the following description.

DETAILED DESCRIPTION

Figure 1:
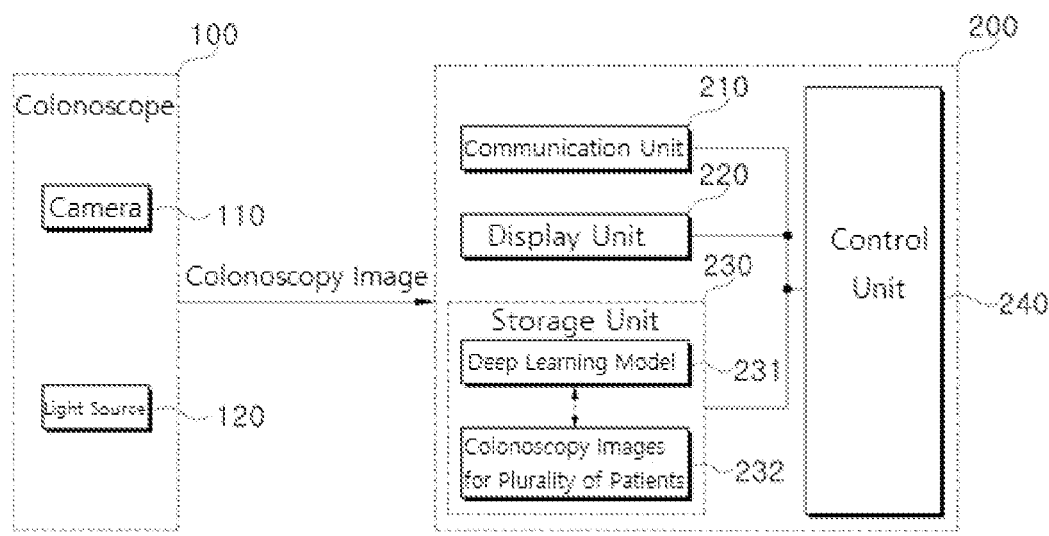
FIG. 1 is a block diagram of a system including a device for detecting colon polyps through AI-based blood vessel learning according to an embodiment of the present disclosure.

The advantages and features of the present disclosure and methods of achieving them will be apparent from the embodiments that will be described in detail with reference to the accompanying drawings. It should be noted, however, that the present disclosure is not limited to the following embodiments, and may be implemented in various different forms. Rather the embodiments are provided so that this disclosure will be thorough and complete and will fully convey the scope of the present disclosure to those skilled in the technical field to which the present disclosure pertains, and the present disclosure will only be defined by the appended claims.

Terms used in the specification are used to describe embodiments of the present disclosure and are not intended to limit the scope of the present disclosure. In the specification, the terms in singular form may include plural forms unless otherwise specified. The expressions "comprise" and/or "comprising" used herein indicate the existence of one or more other elements other than stated elements but do not exclude presence of additional elements. Like reference denotations refer to like elements throughout the specification. As used herein, the term "and/or" includes each and all combinations of one or more of the mentioned elements. It will be understood that, although the terms "first", "second", or the like, may be used herein to describe various elements, these elements should not be limited by these terms. These terms are only used to distinguish one element from another element. Accordingly, a first element mentioned below could be termed a second element without departing from the technical ideas of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Spatially relative terms, such as "below," "beneath," "lower," "above," "upper," and the like, may be used for ease of description to describe a relationship between one component and another components as illustrated in the drawings. Spatially relative terms may be intended to encompass different orientations of the components in use or operation in addition to the orientation illustrated in the drawings. For example, if the component illustrated in the drawings is turned over, components described as "below" or "beneath" other components would then be oriented "above" the other components. Accordingly, the example term "below" can encompass both an orientation of above and below. The component may also be oriented in a different orientation, and accordingly, the spatially relative terms may be interpreted according to the orientation.

Like reference numerals refer to like elements throughout the specification of the present disclosure. This disclosure does not describe all elements of embodiments, and a general description in the technical field to which the present disclosure pertains or a repetitive description in the embodiments will be omitted. As used herein, the term "unit," "module," "member," or "block" may be implemented as software or hardware. Depending on embodiments, a plurality of "units," "modules," "members," or "blocks" may be implemented as one element, or one "unit," "module," "member," or "block" may include a plurality of elements.

In addition, when a certain portion "comprises or includes" a certain component, this indicates that the other components are not excluded and may be further included unless specially described otherwise.

In each operation, reference numerals are used for the sake of convenience in description, and such reference numerals do not describe the order of each operation. The order of each operation may vary from the specified order, unless the context clearly indicates a specific order.

In the present disclosure, a control unit 240 may be known as a processor, a controller, a microcontroller, a microprocessor, and a microcomputer, and may control the overall organic operation of a communication unit 210, a display unit 220, and a storage unit 230. The control unit 240 may refer to an element that performs various determinations and calculations, and may be implemented by hardware or firmware, software, or a combination thereof.

Hereinafter, embodiments of the present disclosure will be described in detail with reference to the accompanying drawings.

FIG. 1 is a block diagram of a system including a device for detecting colon polyps through AI-based blood vessel learning according to an embodiment of the present disclosure, and includes a colonoscope 100 and a device 200 for detecting colon polyps.

The colonoscope 100 includes a camera 110 and a light source 120, and the device 200 for detecting colon polyps includes a communication unit 210, a display unit 220, a storage unit 230, and a control unit 240.

Figure 2:
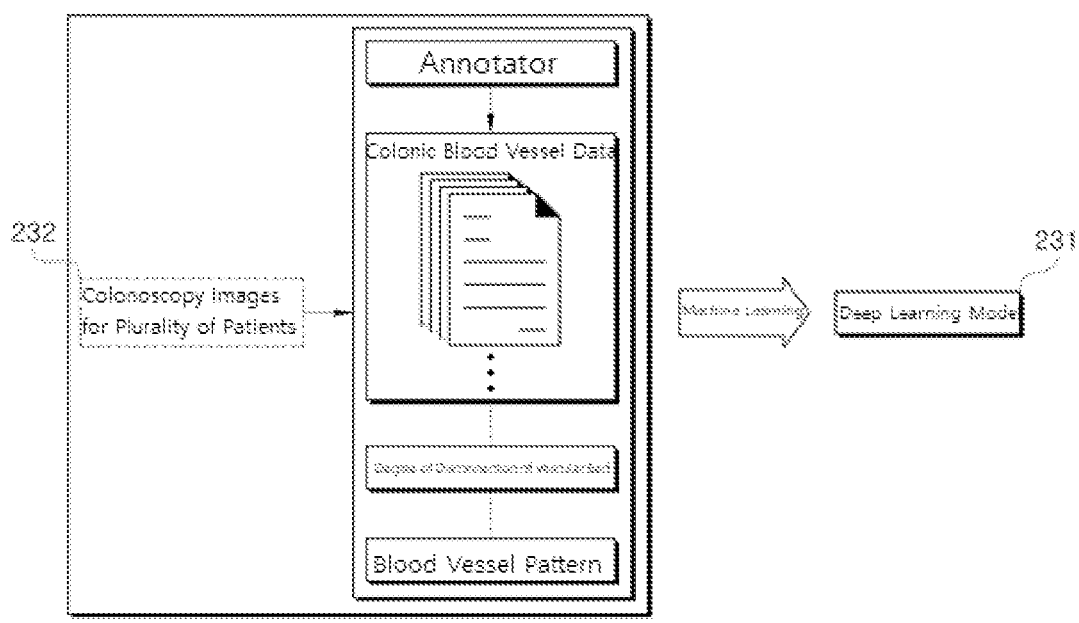
FIG. 2 is a block diagram schematically illustrating that a deep learning model used for detecting colon polyps through AI-based blood vessel learning according to an embodiment of the present disclosure has learned.
Figure 3A:
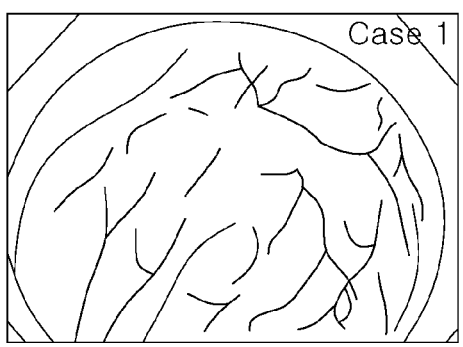
FIGS. 3A-3D are exemplary diagrams illustrating that colonic mucosa in which thin-film planar polyps are hidden in an endoscopic image captured according to an embodiment of the present disclosure is displayed for each of four cases.
Figure 3B:
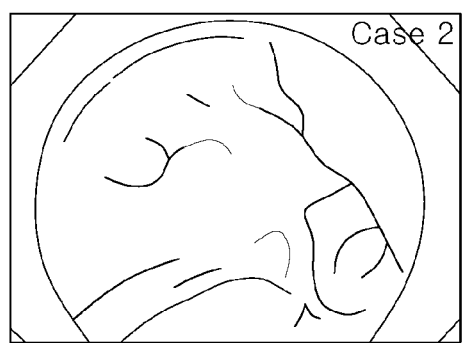
Figure 3C:
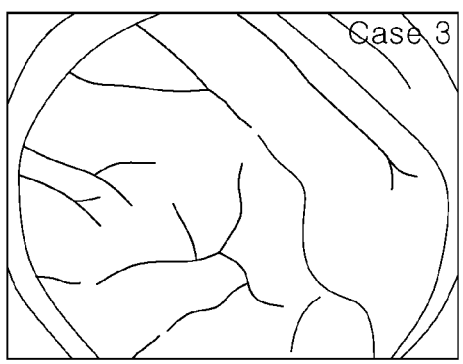
Figure 3D:
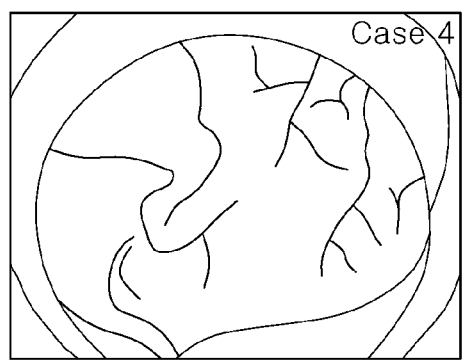

FIG. 2 is a block diagram schematically illustrating that a deep learning model used for detecting colon polyps through AI-based blood vessel learning according to an embodiment of the present disclosure is learned.

FIGS. 3A-3D are exemplary diagrams illustrating that colonic mucosa in which thin-film planar polyps are hidden in an endoscopic image captured according to an embodiment of the present disclosure is displayed for each of four cases.

FIGS. 4A-4D are exemplary diagrams illustrating that a display line is additionally displayed in the exemplary diagrams for each of the four cases illustrated in FIGS. 3A-3D.

Figure 5:
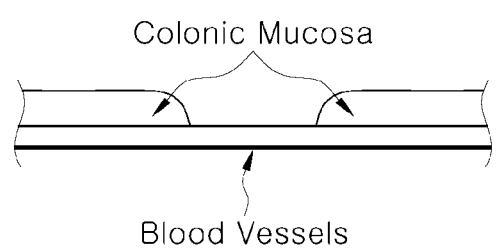
FIG. 5 is a cross-sectional diagram of the colon wall illustrating a difference in a degree of blood vessels visible according to an embodiment of the present disclosure.

FIG. 5 is a cross-sectional diagram of the colon wall illustrating a difference in a degree of blood vessels visible according to an embodiment of the present disclosure.

Figure 6:
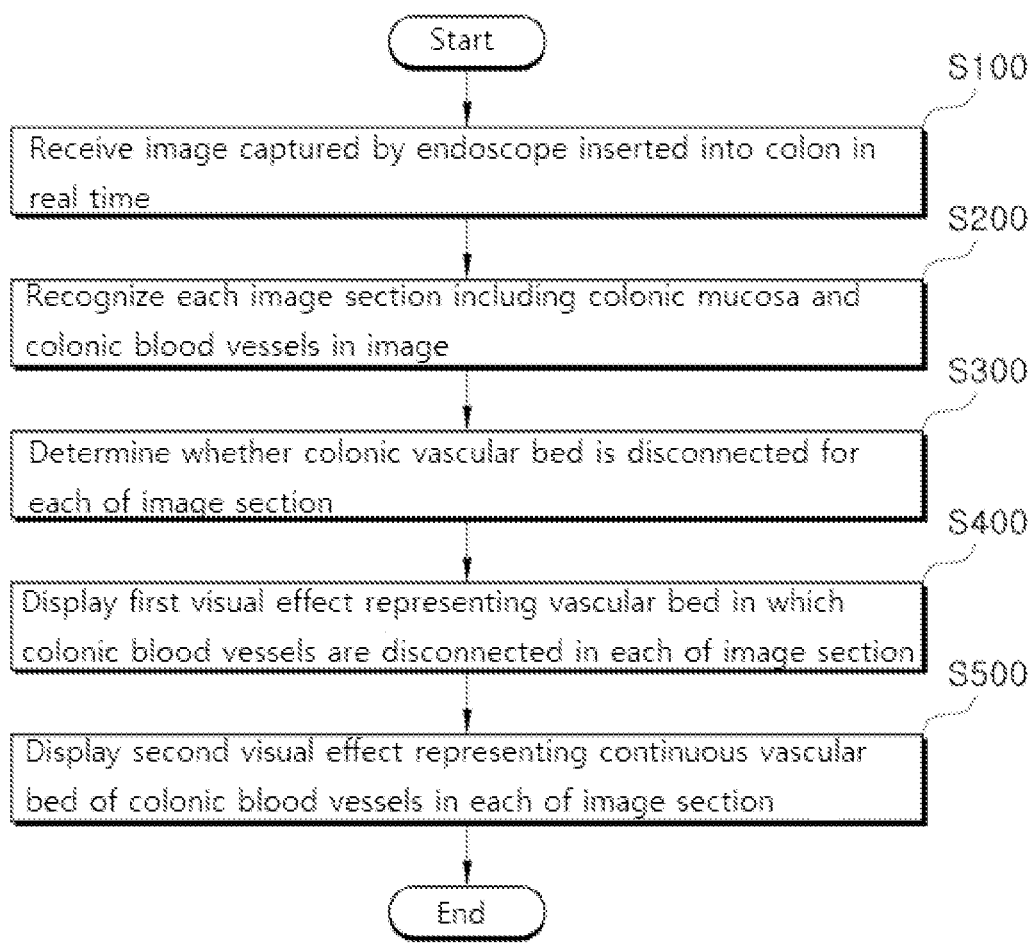
FIG. 6 is a flowchart illustrating an overall operation of a method of detecting colon polyps through AI-based blood vessel learning according to another embodiment of the present disclosure.

FIG. 6 is a flowchart illustrating an overall operation of a method of detecting colon polyps through AI-based blood vessel learning according to another embodiment of the present disclosure.

An organic operation of a method of detecting colon polyps through AI-based blood vessel learning according to an embodiment of the present disclosure will be described in detail with reference to FIGS. 1 to 6.

Deep learning is a class of machine learning based on an artificial neural network in which machines learn by mimicking human biological neurons.

In deep learning technology, a diagnostic model for diagnosing a disease is formed by repeatedly learning learning data. Since the types of diseases used as learning data are diverse, it is important to develop a diagnostic model specialized for each disease.

Accordingly, in the present disclosure, a deep learning algorithm is used to recognize polyps by analyzing images of colons and displaying a location in which a vascular bed is suddenly disconnected as a location in which there is a possibility that thin and flat thin-film planar polyps exist.

In the deep learning algorithm of the present disclosure, AI that has learned the shape of a colic vasculature detects a pattern in which a vascular bed located on a lower side of the colonic mucosa is disconnected centered on a marker line, which is a kind of marker, and discriminates the same as a suspicious lesion.

In other words, the device 200 for detecting colon polyps recognizes the disconnected vascular bed centered on a marker line in a colonoscopy image when the colonoscopy is performed, and provides the image to a colonoscopy tester.

Thereby, it is possible to easily find thin-film planar polyps existing in a thin and flat shape on the colonic mucosa.

The device 200 for detecting colon polyps displays different visual effects for each vascular bed cut off centered on a marker line recognized in the colonoscopy image, so that when a degree of visible blood vessels is large, the entire blood vessels are induced to be checked without checking and passing over only a part of the blood vessels located on a lower side of the colonic mucosa.

Thereby, it is possible to clearly determine the presence of polyps existing in a thin and flat shape on the colonic mucosa.

Referring to FIG. 1, the colonoscope 100 is a device that is inserted into the colon to observe living tissues in the colon, and includes the camera 110, the light source 120, and the like.

In addition, the device 200 for detecting colon polyps includes the communication unit 210, the display unit 220, the storage unit 230, and the control unit 240.

The communication unit 210 may include one or more modules enabling wireless communication between the device 200 for detecting colon polyps and a wireless communication system, between the device 200 for detecting colon polyps and the colonoscope 100, or between the device 200 for detecting colon polyps and an external device (not shown).

The communication unit 210 may receive an endoscopic image captured by the colonoscope 100 inserted into the colon of a test subject, receive an image captured by the colonoscope 100 inserted into the colons of a plurality of test subjects, or receive an image captured by the colonoscope 100 inserted into the colon several times for one test subject.

The communication unit 210 may receive an annotator for an image of the colon of a test subject captured through the colonoscope 100 for learning the deep learning model 231, for example, blood vessel data located on a lower side of the colonic mucosa obtained from a medical staff.

The display unit 220 may be implemented as a touchscreen by forming a layer structure with a touch sensor or being formed integrally with the touch sensor.

Such a touchscreen provides an input interface between the device 200 for detecting colon polyps and a user, and simultaneously provides an output interface between the device 200 for detecting colon polyps and the user.

The display unit 220 may display various pieces of information generated by the control unit 240 and provide the same to a user, and simultaneously receive various pieces of information from the user.

In more detail, the display unit 220 may display a first visual effect representing a vascular bed in which the colonic blood vessels located on a lower side of the colonic mucosa are disconnected for each section of the endoscopic image received from the communication unit 210.

In addition, the display unit 220 may display a second visual effect representing a continuous vascular bed without the colonic blood vessels being disconnected in each image section.

The storage unit 230 may store information supporting various functions of the device 200 for detecting colon polyps.

The storage unit 230 may store a plurality of application programs (or applications) driven in the device 200 for detecting colon polyps, data for the operation of the device 200 for detecting colon polyps, and commands.

At least some of these application programs may be downloaded from an external server (not shown) through wireless communication. In addition, at least some of these application programs may exist for a basic function of the device 200 for detecting colon polyps.

The application program may be stored in the storage unit 230, installed on the device 200 for detecting colon polyps, and driven to perform the operation (or function) of the device 200 for detecting colon polyps by the control unit 240.

The storage unit 230 may store a deep learning model 231 for recognizing blood vessels located on a lower side of the colonic mucosa in the image captured by the colonoscope 100 inserted into the colon of a test subject.

Herein, the deep learning model 231 may include a convolutional neural network (hereinafter referred to as CNN), but is not necessarily limited thereto and may be formed of a neural network of various structures.

The CNN may be formed in a structure in which a convolution layer that creates a feature map by applying a plurality of filters to each area of an image and a pooling layer enabling to extract a feature which is not changed over a change in position or rotation by spatially integrating the feature map are alternately repeated several times.

This enables extraction of various levels of features from a low-level feature such as a point, a line, a surface, or the like to a complex and meaningful high-level feature.

The convolution layer obtains a feature map by taking a nonlinear activation function to an inner product of a filter and a local receptive field for each patch of an input image.

Compared with other network structures, the CNN uses a filter having shared weights and sparse connectivity.

This connection structure reduces the number of parameters to be trained and makes training through a backpropagation algorithm efficient, resulting in improved prediction performance.

In this way, a feature that was finally extracted via repetition of the convolution layer and the pooling layer may be combined with a classification model such as Multi-Layer Perception (MLP) or Support Vector Machine (SVM) in a form of the fully-connected layer and thus may be used for learning and prediction of the classification model.

The storage unit 230 may store the colonoscopy image received through the communication unit 210.

In addition, the storage unit 230 may store an image captured by the colonoscope 100 inserted into the colons of a plurality of test subjects or an image captured by the colonoscope 100 inserted into the colon of one test subject several times.

In addition, the storage unit 230 may store an annotator for an image of the colon of a test subject captured through the colonoscope 100 for learning the deep learning model 231, for example, blood vessel data obtained from a medical staff.

In addition to the operation related to the application program, the control unit 240 may generally control an overall operation of the device 200 for detecting colon polyps.

The control unit 240 may process signals, data, information, or the like input or output through the aforementioned components or drive an application program stored in the storage unit 230 to provide or process appropriate information or functions to a user.

The control unit 240 controls the operation of the components illustrated in FIG. 1, that is, the communication unit 210, the display unit 220, and the storage unit 230 in order to drive the application program stored in the storage unit 230.

Hereinafter, the operation of the control unit 240 will be described in detail as follows.

The control unit 240 may recognize an image of each section of an inner wall of the colon based on the deep learning model 231 in the image captured by the colonoscope 100 inserted into the colon of a test subject.

In other words, the control unit 240 may recognize blood vessels located on a lower side of the colonic mucosa in each image section, and identify a difference in a degree of visible blood vessels.

As illustrated in FIGS. 1 and 2, the control unit 240 recognizes each image section through the deep learning model 231. The deep learning model 231 may be a machine-learning model based on blood vessel data in colonic images of a plurality of test subjects obtained from external annotators, and a degree of disconnection of a vascular bed due to light irradiated into an interior of the colon and a blood vessel pattern.

Specifically, the control unit 240 may obtain at least one image captured at least once from the colonoscope 100 inserted into the colons of a plurality of test subjects, and obtain blood vessel data from an annotator for each of the plurality of images.

Herein, the annotator may be an expert who may well identify the blood vessels of the colon, and the plurality of images may be an image of an endoscope performed several times for one subject, or an image of an endoscope performed for a plurality of test subjects.

Thereafter, the control unit 240 may perform machine learning based on a degree of disconnection of a vascular bed on an inside of the colon and blood vessel data.

Herein, a degree of disconnection of a vascular bed may be created by determining whether the degree of disconnection of a vascular bed that the control unit 240 sees according to the light irradiated into an inner wall of the colon from the light source 120 of the colonoscope 100 changes by more than a preset percentage threshold value.

Specifically, the control unit 240 may determine that there is a polyp on the site, when the degree of disconnection of the vascular bed is greater than or equal to a preset percentage threshold value.

In addition, the control unit 240 may recognize a blood vessel pattern formed by blood vessels in an endoscopic image of the colon, and recognize an area having a polyp in the endoscopic image of the colon based on the recognized blood vessel pattern.

In detail, the control unit 240 may recognize at least one blood vessel pattern in an endoscopic image of the colon generated by light irradiated into an inner wall of the colon from the light source 120 of the colonoscope 100, and recognize an area having a polyp in the endoscopic image of the colon based on the recognized blood vessel pattern.

The control unit 240 may set a section from the point where the colonoscope 100 is inserted to the point identified according to the light irradiated into an interior of the colon by the light source 120 provided in the colonoscope 100 as one section.

In other words, the control unit 240 may divide the colon into n sections to recognize the colonic blood vessels for each section.

Herein, an adult colon is about 150 cm to 170 cm, and the distance to a point identified according to the light irradiated from the light source 120 provided in the colonoscope 100 may be approximately 10 cm to 15 cm.

Accordingly, the control unit 240 may divide the colon into approximately 10 to 15 sections, and recognize a presence of polyps for each section.

Specifically, the control unit 240 may create the point at which the colonoscope 100 is inserted and the point identified according to the light irradiated into an interior of the colon by the light source 120 provided in the colonoscope 100 based on the deep learning model 231.

The control unit 240 may display a first visual effect representing a vascular bed image in which the colonic blood vessels are disconnected in each image section.

The control unit 240 may display a second visual effect representing a continuous vascular bed without the colonic blood vessels being disconnected in each image section.

The first visual effect may include a visual effect in which each marker is displayed on an inner wall of the corresponding colon in each image section.

The length of each marker may be determined based on a degree of disconnection of the corresponding vascular bed.

Thereafter, the control unit 240 may display a first visual effect on the presence and length of the marker to make it easier for a specialist surgeon to check the presence and size of thin, flat, thin-film planar polyps on the colonic mucosa.

The colonoscope 100 may move into the colon while checking whether a vascular bed in the colon is disconnected one by one according to the first and second visual effects in a plurality of sections.

Specifically, after the colonoscope 100 recognizes a degree of disconnection of a vascular bed for each area, it returns to the starting point where the area starts for each area, and then it may be checked without omission for each area.

Figure 4A:
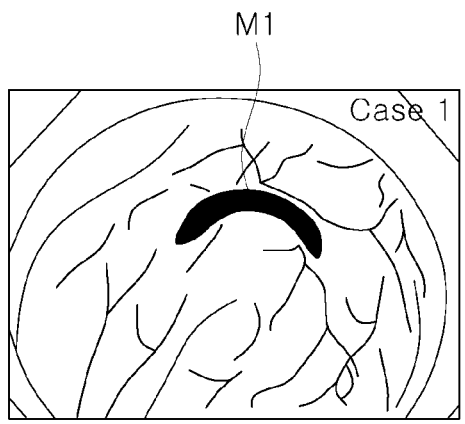
FIGS. 4A-4D are exemplary diagrams illustrating that a display line is additionally displayed in the exemplary diagrams for each of the four cases illustrated in FIGS. 3A-3D.

For example, referring to FIG. 4A, the control unit 240 may display a first visual effect as an image in which a vascular bed is disconnected centered on a first marker M1 displayed by a curve extending in a transverse direction in a first section.

Figure 4B:
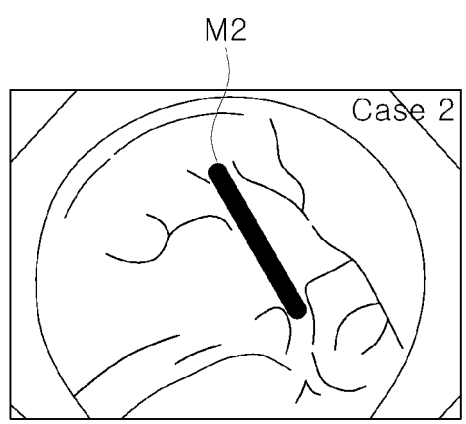

Referring to FIG. 4B, the control unit 240 may display a first visual effect as an image in which a vascular bed is disconnected centered on a second marker M2 displayed by a straight line extending in a diagonal direction in a second section.

Figure 4C:
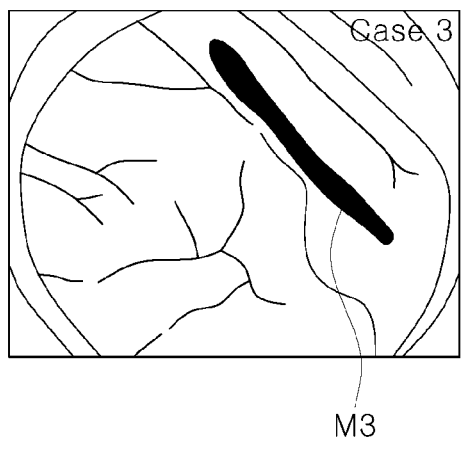

Referring to FIG. 4C, the control unit 240 may display a first visual effect as an image in which a vascular bed is disconnected in a third section centered on a third marker M3 displayed by a straight line extending in a diagonal direction longer than the second marker M2 in the second section.

Figure 4D:
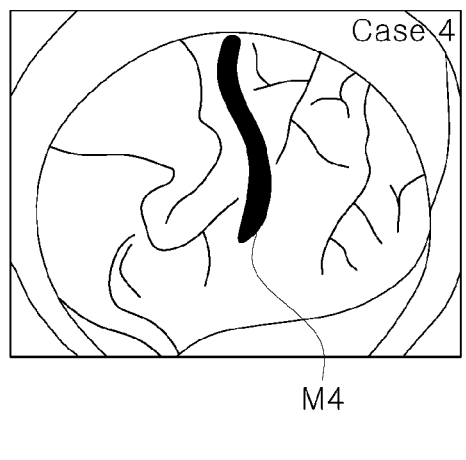

Referring to FIG. 4D, the control unit 240 may display a first visual effect as an image in which a vascular bed is disconnected centered on a fourth marker M4 displayed by a curve extending in a vertical direction in a second section.

In addition, the control unit 240 may display a second visual effect representing a continuous vascular bed without the colonic blood vessels being disconnected in each image section.

Accordingly, the control unit 240 surely provides a first visual effect for abnormal colon lesions where thin, flat, thin-film planar polyps are hidden when a specialist surgeon reads a colon disease through the colonoscope 100 or a second visual effect for a normal colonic inner wall. Hence, it is possible to increase the accuracy of colon examination by allowing all thin and flat polyps to be checked without polyps that cannot be identified.

FIG. 6 is a flowchart illustrating an overall operation of a method of detecting colon polyps through AI-based blood vessel learning according to another embodiment of the present disclosure.

The control unit 240 recognizes each image section including the colonic mucosa and the colonic blood vessels in an image captured by the colonoscope 100 inserted into the colon of a test subject (S200) received in real time through the communication unit 210 (S100).

Herein, the control unit 240 recognizes each image section including the colonic mucosa and the colonic blood vessels based on the light irradiated into an interior of the colon by the colonoscope 100.

In addition, the control unit 240 recognizes each image section through the deep learning model 231.

Herein, the deep learning model 231 may be a machine-learning model based on blood vessel data in colonic images of a plurality of test subjects obtained from external annotators, and a degree of disconnection of a vascular bed due to light irradiated into an interior of the colon and a blood vessel pattern.

The control unit 240 determines whether a colonic vascular bed is disconnected for each image section (S300).

As a result of the determination, the control unit 240 displays, on the display unit 220, a first visual effect representing a vascular bed in which the colonic blood vessels are disconnected in each image section (S400).

The first visual effect includes a visual effect in which each marker is displayed on the corresponding vascular bed in which the colonic blood vessels are disconnected in each image section, and the size of each of the markers may be determined based on a degree of disconnection of the corresponding vascular bed.

As a result of the determination, the control unit 240 displays, on the display unit 220, a second visual effect representing a continuous vascular bed without the colonic blood vessels being disconnected in each image section (S500).

The control unit 240 provides a presence and size of thin and flat thin-film planar polyps on the colonic mucosa through the first visual effect and an absence of the polyps on the colonic mucosa through the second visual effect displayed on the display unit 220 so that a specialist surgeon can easily see.

Although FIG. 6 illustrates that the operations S100 to S500 are sequentially carried out, they are merely exemplifying the technical idea of the present embodiment. It will be appreciated by a person having ordinary skill in the technical field to which the present embodiment pertains that various modifications and variations may be made without departing from the essential features of the present embodiment such that the sequence illustrated in FIG. 6 is changed and carried out, or one or more operations are carried out in parallel. Thus, FIG. 6 is not limited to a sequence in time series.

Thereby, it is possible to significantly lower the probability of missing abnormal colon lesions where thin, flat, thin-film planar polyps are hidden when reading a colon disease.

In addition, even a colonoscopy tester with low test proficiency can detect and excise thin, flat, thin-film planar polyps with high accuracy when a method of detecting colon polyps of the present disclosure is utilized.

As such, the present disclosure provides a method and device for detecting colon polyps through AI-based blood vessel learning, wherein the method uses AI that has learned the shape of a colic vasculature to detect a pattern in which a vascular bed seen between the colonic mucosa is disconnected centered on a marked line and discriminate the same as a suspicious lesion.

According to the present disclosure, when reading a colon disease through a colonoscopy image, even a colonoscopy tester with low test proficiency will be able to detect and excise polyps with high accuracy for abnormal colon lesions where thin, flat, thin-film planar polyps existing on the colonic mucosa are hidden.

The method according to an embodiment of the present disclosure described above may be implemented as a program (or an application) to be executed in combination with a server, which is hardware, and stored in a medium.

The above-described program may include a code encoded by a computer language such as C, C++, JAVA, or a machine language, which a processor (CPU) of the computer can read through a device interface of the computer, such that the computer reads the program and performs the methods implemented with the program. The code may include functional codes associated with the function that defines functions necessary to perform the methods, and may include a control code associated with an execution procedure necessary for the processor of the computer to perform the functions in a predetermined procedure. Furthermore, the code may further include additional data necessary for the processor of the computer to perform the functions or a memory reference-related code associated with the location (address) of the internal or external memory of the computer, at which the media needs to be referred. In addition, when the processor of the computer needs to communicate with any other remote computer or any other remote server to perform the functions, the code may further include a communication-related code associated with how to communicate with any other remote computer or server using the communication module of the computer, and what data or media should be transmitted or received during communication.

The storing media may mean the media that does not store data for a short period of time such as a register, a cache, a memory, or the like but semi-permanently stores to be read by the device. Specifically, for example, the storing media include, but are not limited to, ROM, RAM, CD-ROM, magnetic tape, floppy disk, optical data storage device, and the like. That is, the program may be stored in various recording media on various servers that the computer can access, or various recording media on the computer of the user. In addition, the media may be distributed to a computer system connected to a network, and a computer-readable code may be stored in a distribution manner.

The steps of a method or algorithm described in connection with the embodiments of the present disclosure may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form well known in the technical field to which the present disclosure pertains.

Although the embodiments of the present disclosure have been described with reference to the attached drawings, those skilled in the technical field to which the present disclosure pertains will understand that the present disclosure may be practiced in other detailed forms without departing from the technical spirit or essential features of the present disclosure. Therefore, it should be understood that the above-described embodiments are exemplary in all aspects rather than being restrictive.

DRAWINGS

100: COLONOSCOPE
110: CAMERA
120: LIGHT SOURCE
200: DEVICE FOR DETECTING COLON POLYPS
210: COMMUNICATION UNIT
220: DISPLAY UNIT

230: STORAGE UNIT
240: CONTROL UNIT

The invention claimed is:

1. A method of detecting colon polyps through artificial intelligence-based blood vessel learning, wherein the method is performed by a device and includes:
   (a) receiving an image captured by an endoscope inserted into colon of a test subject in real time;
   (b) recognizing each image section including colonic mucosa and colonic blood vessels in the image;
   (c) determining whether a colonic vascular bed is disconnected in each image section;
   (d) displaying a first visual effect representing a vascular bed in which the colonic blood vessels are disconnected in each image section; and
   (e) displaying a second visual effect representing a continuous vascular bed of the colonic blood vessels in each image section,
   wherein operation (b) is configured to recognize each image section through a deep learning model, and
   wherein the deep learning model is a machine-learning model based on blood vessel data in a plurality of colonic images of the test subject obtained from external annotators, and a degree of disconnection of the vascular bed due to light irradiated into an interior of the colon and a blood vessel pattern.

2. The method of claim 1, wherein the first visual effect includes a visual effect in which each marker is displayed on the corresponding vascular bed in which the colonic blood vessels are disconnected in each image section.

3. The method of claim 2, wherein a size of each of the markers is determined based on a degree of disconnection of the corresponding vascular bed.

4. The method of claim 3, wherein in operation (c), whether the colonic vascular bed is disconnected is determined based on whether a degree of disconnection of the corresponding vascular bed changes by more than a preset percentage threshold value, and when the degree of disconnection of the vascular bed is greater than or equal to the preset percentage threshold value, the control unit determines that there is a thin-film planar polyp on a corresponding area on the colonic mucosa.

5. The method of claim 1, wherein a control unit is configured to determine a presence and size of thin-film planar polyps on colonic mucosa through the first visual effect, and determine an absence of the thin-film planar polyps on the colonic mucosa through the second visual effect.

6. A computer program combined with a computer, which is hardware, and stored in a computer-readable recording medium in order to perform the method of detecting colon polyps through artificial intelligence-based blood vessel learning according to claim 1.

7. A device for detecting colon polyps through artificial intelligence-based blood vessel learning, the device including:
   a display unit;
   a communication unit receiving an image captured by an endoscope inserted into colon of a test subject in real time;
   a storage unit storing the received image and a deep learning model for recognizing colonic blood vessels in the received image; and
   a control unit recognizing each image section including colonic mucosa and colonic blood vessels in the received image through the deep learning model, displaying, on the display unit, a first visual effect representing a vascular bed in which the colonic blood vessels are disconnected in each image section, and displaying, on the display unit, a second visual effect representing a continuous vascular bed of the colonic blood vessels in each image section,
   wherein the deep learning model is a machine-learning model based on blood vessel data in a plurality of colonic images of the test subject obtained from external annotators, and a degree of disconnection of the vascular bed due to light irradiated into an interior of the colon and a blood vessel pattern.

8. The device of claim 7, wherein the first visual effect includes a visual effect in which each marker is displayed on the corresponding vascular bed in which the colonic blood vessels are disconnected in each image section, and a size of each of the markers is determined based on a degree of disconnection of the corresponding vascular bed.

9. The device of claim 8, wherein the control unit determines whether the colonic vascular bed is disconnected based on whether a degree of disconnection of the corresponding vascular bed changes by more than a preset percentage threshold value, and when the degree of disconnection of the vascular bed is greater than or equal to the preset percentage threshold value, the control unit determines that there is a thin-film planar polyp on a corresponding area on the colonic mucosa.

10. The device of claim 7, wherein the control unit is configured to determine a presence and size of thin-film planar polyps on colonic mucosa through the first visual effect, and determine an absence of the thin-film planar polyps on the colonic mucosa through the second visual effect.

* * * * *